United States Patent [19]

Hatano et al.

[11] Patent Number: 5,128,299
[45] Date of Patent: Jul. 7, 1992

[54] PROCESS FOR PRODUCING CRYSTALLINE OXIDE OF VANADIUM-PHOSPHORUS SYSTEM

[75] Inventors: Masakatsu Hatano; Masayoshi Murayama; Kenji Shima; Masumi Ito, all of Yokohama, Japan

[73] Assignee: Mitsubishi Kasei Corporation, Tokyo, Japan

[21] Appl. No.: 623,091

[22] Filed: Dec. 6, 1990

Related U.S. Application Data

[62] Division of Ser. No. 414,313, Sep. 29, 1989, Pat. No. 5,021,384.

[30] Foreign Application Priority Data

Oct. 5, 1988 [JP] Japan ................. 63-249953
Aug. 10, 1989 [JP] Japan ................. 1-205570

[51] Int. Cl.⁵ ................. B01J 27/198; B01J 31/32; C07D 307/60
[52] U.S. Cl. ................. 502/209; 502/210; 502/213; 549/259; 549/260
[58] Field of Search ............. 502/209, 210, 213, 150, 502/167, 172; 423/305, 306

[56] References Cited

U.S. PATENT DOCUMENTS

| | | | |
|---|---|---|---|
| 3,888,886 | 6/1975 | Young et al. | 549/259 |
| 3,975,300 | 8/1976 | Burress | 502/209 |
| 4,127,591 | 11/1978 | Kamimura et al. | 502/209 |
| 4,337,174 | 6/1982 | Mount et al. | 502/209 |
| 4,380,648 | 5/1983 | Udovich et al. | 549/259 |
| 4,435,521 | 3/1984 | Yang et al. | 502/209 |
| 4,472,527 | 9/1984 | Otake et al. | 502/209 |
| 4,520,127 | 5/1985 | Otake et al. | 502/209 |
| 4,652,543 | 3/1987 | Edwards et al. | 502/209 |
| 5,021,384 | 6/1991 | Hatano et al. | 502/209 |

FOREIGN PATENT DOCUMENTS

| | | | |
|---|---|---|---|
| 71544 | 4/1987 | Japan | 502/209 |
| 2118060 | 10/1983 | United Kingdom . | |

Primary Examiner—Paul E. Konopka
Attorney, Agent, or Firm—Oblon, Spivak, McClelland, Maier & Neustadt

[57] ABSTRACT

A process for producing a crystalline oxide of vanadium-phosphorus system, which comprises hydrothermally treating an aqueous medium containing (1) a tetravalent vanadium compound, (2) a pentavalent phosphorus compound, (3) a coordinate compound having at least two ligand atoms selected from the group consisting of oxygen atoms and nitrogen atoms and (4) a compound of at least one metal element selected from the group consisting of iron, nickel, cobalt and chromium, to form a crystalline oxide of vanadium-phosphorus system having an X-ray diffraction pattern shown in Table A:

TABLE A

| X-ray diffraction peaks (Anticathode: Cu—Kα) $2\theta$ ($\pm 0.2°$) | | | |
|---|---|---|---|
| 15.6° | 19.7° | | 24.3° |
| 27.2° | 28.8° | 30.5° | 33.8° |

16 Claims, No Drawings

PROCESS FOR PRODUCING CRYSTALLINE OXIDE OF VANADIUM-PHOSPHORUS SYSTEM

This is a division of application Ser. No. 07/414,313, filed on Sep. 29, 1989, now U.S. Pat. No. 5,021,384.

The present invention relates to a crystalline oxide of vanadium-phosphorus system, a process for its production, a catalyst containing such an oxide, use of the catalyst as a catalyst for the production of maleic anhydride and a process for the production of the catalyst. More particularly, the present invention relates to an oxide catalyst useful for the production of maleic anhydride by the gas phase catalytic oxidation reaction of a hydrocarbon having at least 4 carbon atoms, a process for its production and use of the catalyst as a catalyst for the production of maleic anhydride.

Compound oxides of vanadium-phosphorus system are widely known as catalyst components useful for the production of maleic anhydride by a gas phase catalytic oxidation reaction of a hydrocarbon having at least 4 carbon atoms. In particular, a crystalline oxide of vanadium-phosphorus system having an X-ray diffration pattern shown in Table B (hereinafter referred as a calcined oxide) is known as an active component of a catalyst for the production of maleic anhydride by the gas phase oxidation of a paraffin or olefin hydrocarbon having 4 carbon atoms such as butane or butene.

TABLE B

| X-ray diffraction peaks (Anticathode: Cu—Kα) $2\theta$ ($\pm 0.2°$) | | |
|---|---|---|
| 14.2° | 15.7° | 18.5° |
| 23.0° | 28.4° | 30.0° |
| 33.7° | 36.8° | |

This calcined oxide is known to be a compound called divanadyl pyrophosphate $(VO)_2P_2O_7$ [E. Bordes, P. Courtine, J. Catal., 57, 236-252, (1979)].

Many methods have been reported for the production of this compound. Commonly, this compound is prepared by calcining a crystalline oxide of vanadium-phosphorus system having an X-ray diffraction pattern shown in Table A (hereinafter referred to as a precursor oxide).

TABLE A

| X-ray diffraction peaks (Anticathode: Cu—Kα) $2\theta$ ($\pm 0.2°$) | | | |
|---|---|---|---|
| 15.6° | | 19.7° | 24.3° |
| 27.2° | 28.8° | 30.5° | 33.8° |

When calcined, the precursor oxide discharges water of crystallization and undergoes rearrangement, and is thus converted to divanadyl pyrophosphate i.e. the calcined oxide [E. Bordes et al, Mater. Sci. Monograph, 28B, 887-892 (1985)]. (This is the reason why the former is referred to as a precursor oxide, and the latter is referred to as a calcined oxide.)

The precursor oxide has also been analyzed by X-ray structural analysis and has been reported to be represented by $VO(HPO_4)\cdot\frac{1}{2}H_2O$ [J. W. Johnson et al, J. Am. Chem. Soc., 106, 8123-8128 (1984) or by $(VO)_2H_4P_2O_9$ [C. C. Torardi et al, Inorg. Chem., 23, 1308-1310 (1984)]. When the calcined oxide is prepared by using the precursor oxide as the starting material, the physical properties and activities of the calcined oxide are substantially influenced by the structure of the precursor oxide, hence by the production conditions of the precursor oxide.

Heretofore, various methods have been proposed for the preparation of the precursor oxide. For example, the following methods are known:

(1) A method wherein a pentavalent vanadium compound such as vanadium pentoxide is reduced in a non-oxidative acidic solution such as a hydrochloric acid solution, if necessary, by using a reducing agent such as oxalic acid, to prepare a solution containing tetravalent vanadium ions, then the solution is reacted with phosphoric acid, and the resulting soluble vanadium-phosphorus complex is precipitated by an addition of water (Japanese Unexamined Patent Publication No. 95990/1976);

(2) A method wherein a pentavalent vanadium compound such as vanadium pentoxide and phosphoric acid are reacted in an aqueous medium in the presence of a reducing agent such as hydrazine hydrochloride or hydroxyl amine hydrochloride, followed by concentration or evaporation to dryness to obtain crystals (Japanese Unexamined Patent Publication No. 45815/1981);

(3) A method in which vanadium pentoxide is reduced in an organic medium such as ethanol, isopropanol or glycerol, followed by the reaction with phosphoric anhydride, and if necessary, crystals are precipitated while maintaining the system substantially in an anhydrous state by a combination of azeotropic dehydration with a solvent such as benzene (U.S. Pat. No. 4,283,288, etc.); and (4) A method wherein a solution in an aqueous medium of a tetravalent vanadium compound and a pentavalent phosphorus compound, is hydrothermally treated to form crystals (Japanese Unexamined Patent Publication No. 32110/1982).

Among them, the method (4) is industrially excellent with such advantages that a precursor oxide having excellent crystallinity with (020) face well developed is thereby obtainable, the method can be conducted in a non-corrosive atmosphere and it is thereby possible to avoid problems of e.g. treatment of inflammables or wastes.

Further, it has been reported that in the production of a catalyst containing an oxide of vanadium-phosphorus system, it is possible to improve the catalytic activities such as lowering of the reaction temperature and improvement of the yield of the maleic anhydride by using a compound of iron, cobalt, nickel, chromium or the like as an accelerator in the gas phase catalytic oxidation reaction [B. K. Hodnet, Catal. Rev., 27, 373-424 (1985), and Japanese Examined Patent Publication No. 12496/1978].

The addition of such an accelerator component is usually conducted by adding the metal compound before or after the reaction of the vanadium compound and the phosphorus compound and finally permitting it to coprecipitate, or by a technique wherein the metal compound is impregnated to a compound oxide of vanadium-phosphorus system. Such addition is considered to be a practically effective method for catalyst modification.

However, the addition of such an accelerator component can be effective only in the case of the method of reducing vanadium in the organic medium or the method of reducing vanadium in an aqueous hydrochloric acid solution, followed by evaporation to dryness, among the above-mentioned various methods for the production of the precursor oxide. In the case of the hydrothermal treatment method which is industrially superior as a method for the production of the precursor oxide, as mentioned above, its effects are not distinct, and the addition has not been effective. This may probably be attributable to a mechanism such that a thermodynamically stable or almost stable phase is formed by the hydrothermal treatment, whereby the element having the accelerating effects may be hardly taken in the crystals of the compound oxide of vanadium-phosphorus system.

It is an object of the present invention to effectively incorporate the element having the above-mentioned accelerating effects to said oxide during the process for the production of the crystalline oxide of vanadium-phosphorus system by the hydrothermal treatment.

The present inventors have conducted extensive studies on a method of incorporating an element showing excellent accelerating effects to a crystalline oxide of vanadium-phosphorus system produced by hydrothermal treatment. In the course of such studies, the present inventors have tried an experiment wherein the hydrothermal treatment was conducted in the presence of a compound having a chelating property in an attempt to incorporate an effective accelerator component to the crystalline oxide of vanadium-phosphorus system. Specifically, the cation of the vanadium component and the cation of the accelerator component are chelated with a coordinate compound so that they are present close to each other during the hydrothermal treatment, so that they are taken in the crystalline oxide as they are. As a result, it has been found that in a catalyst obtained by the hydrothermal treatment in the presence of a certain chelating agent and an accelerator component, the taking in of the accelerator component takes place, and such a catalyst has improved catalytic activities and is superior in the yield of maleic anhydride as compared with the catalyst made of the crystalline oxide of vanadium-phosphorus system containing no such accelerator component. The present invention has been accomplished on the basis of this discovery.

Namely, the present invention provides a process for producing a precursor oxide, the precursor oxide obtained by the process, a process for producing a calcined oxide, a catalyst containing the precursor oxide, a process for producing a catalyst containing the precursor oxide or the calcined oxide, and use of such a catalyst as a catalyst for the production of maleic anhydride. Namely, the present invention provides a process for producing a crystalline oxide of vanadium-phosphorus system, which comprises hydrothermally treating an aqueous medium containing (1) a tetravalent vanadium compound, (2) a pentavalent phosphorus compound, (3) a coordinate compound having at least two ligand atoms selected from the group consisting of oxygen atoms and nitrogen atoms and (4) a compound of at least one metal element selected from the group consisting of iron, nickel, cobalt and chromium, to form a crystalline oxide of vanadium-phosphorus system having an X-ray diffraction pattern shown in Table A:

TABLE A

| X-ray diffraction peaks (Anticathode: Cu—Kα) $2\theta$ (±0.2°) | | | | |
|---|---|---|---|---|
| 15.6° | | 19.7° | | 24.3° |
| 27.2° | 28.8° | | 30.5° | 33.8° |

(i.e. a precursor oxide); the precursor oxide obtained by the process; a process for producing a calcined oxide which comprises calcining the precursor oxide; a process for producing a catalyst which comprises shaping the precursor oxide into a catalyst form; a catalyst thereby obtained; a process for producing a catalyst which comprises shaping the calcined oxide into a catalyst form; and use of such a catalyst as a catalyst for the production of maleic anhydride by a gas phase catalytic oxidation reaction of a hydrocarbon having at least 4 carbon atoms.

Now, the present invention will be described in detail with reference to the preferred embodiments.

In the present invention, the tetravalent vanadium compound and the pentavalent phosphorus compound are used as starting materials for the basic structure of the oxide of vanadium-phosphorus system. With respect to vanadium, it is possible to use not only a tetravalent compound but also a pentavalent compound as the starting material, as the latter can be reduced to a tetravalent compound with a proper reducing agent.

Specific starting compounds for the vanadium source include pentavalent compounds such as vanadium pentoxide, a metavanadate and vanadium phosphate, and tetravalent compounds such as vanadyl chloride, vanadyl nitrate, vanadyl oxalate and vanadyl dioxide. To use a pentavalent vanadium compound, it is firstly reduced to tetravalent vanadium by means of a proper amount of a known inorganic or organic reducing agent such as hydrazine, hydroxylamine or oxalic acid. Otherwise, it may be refluxed in an excess amount of an organic solvent and then used as a tetravalent vanadium source.

As the phosphorus starting material, an oxide of phosphorus such as phosphoric acid, pyrophosphoric acid, tripolyphosphoric acid or metaphosphoric acid, or its ester, or a compound of pentavalent phosphorus such as phosphorus pentoxide, is usually employed.

When a pentavalent vanadium compound is used as a starting material, it may be subjected to an oxidation reduction reaction by means of a trivalent phosphorus compound such as phosphorous acid or phosphorus trioxide, so that tetravalent vanadium and pentavalent phosphorus will be formed and coexistent.

As the accelerator component, iron, cobalt, nickel and chromium are effective. These elements may be used in the form of inorganic salts such as halides or nitrates, or organic salts such as acetates or oxalates.

The coordinate compound representing the feature of the process of the present invention is a coordinate compound having at least two ligand atoms selected from the group consisting of oxygen atoms and nitrogen atoms. Specifically, it includes primary, secondary and tertiary polyhydric alcohols such as ethylene glycol, 1,4-butanediol, 2,4-pentanediol and pinacol, polyamines such as N,N'-dimethylethylenediamine, 1,10-phenanthroline and N,N'-dimethylimidazole, polybasic organic acids such as tartaric acid, oxalic acid and ethylenediamine tetraacetic acid (EDTA), diketones such as acetylacetone, and amides such as N-methyl-2-pyrrolidone.

With respect to the ratios of the above-mentioned compounds, the atomic ratio of phosphorus/vanadium is within a range of from 0.5 to 2.0, preferably from 0.8 to 1.3, and the atomic ratio of the metal element in the accelerator to vanadium is usually within a range of from 0.001 to 1.0, preferably from 0.01 to 0.20.

The coordinate compound is added in a molar ratio within a range of from 0.01 to 1.0, preferably from 0.1 to 0.5 to vanadium. If the amount is excessive, there will be a problem in the treatment, and the merit of the hydrothermal treatment will be lost.

The above described tetravalent vanadium source, pentavalent phosphorus source, accelerator component and coordinate compound are subjected to hydrothermal treatment, i.e. they are mixed in an aqueous medium and reacted under heating, to obtain the precursor oxide. The concentration of the starting materials for the reaction in the solution is usually preferably within a range of from about 10 to 80%. Here, it is practically effective to add seed crystals, since the crystallization speed can thereby be increased, or the geometrical shape and the particle size of the resulting crystals or the viscosity of the solution can thereby be controlled to some extent. This technique may be employed also for the process of the present invention.

The hydrothermal treatment will now be described in further detail. Starting material compounds such as the vanadium material, the phosphorus material, the optional reducing agent, the coordinate compound and the metal element compound as an accelerator component, are mixed in an aqueous medium and heated in a closed container usually at a temperature of from 110° to 250° C. to obtain the desired precursor oxide. When a compound of pentavalent vanadium is used as a starting material, it is reacted prior to the heating or during the heating so that the valence of the majority of vanadium turns to be tetravalent. The phosphorus material is preferably an oxyacid of pentavalent phosphorus. For the hydrothermal treatment, the total oxide concentration of $V_2O_4 + P_2O_5$ is usually preferably within a range of from 10 to 50% by weight. Particularly preferred is a method wherein vanadium pentoxide is added to an aqueous solution containing phosphorus acid, hydrazine hydrate in a stoichiometric amount required to reduce pentavalent vanadium to tetravalent vanadium, the above-mentioned coordinate compound and the above-mentioned metal element compound, to obtain a vanadium phosphate solution with contaminative ions suppressed to the minimum, and then the hydrothermal treatment is conducted in a closed container usually at temperature of from 110° to 250° C., preferably from 120° to 180° C., usually for from 0.5 to 200 hours. For the above hydrothermal treatment, it is effective to preliminarily add a small amount of seed crystals in the aqueous medium, so that the purity of the resulting crystals of the precursor oxide will be improved.

By conducting the hydrothermal treatment as described above, an aqueous slurry containing grayish blue crystals of the desired precursor oxide can be obtained. The precursor oxide can be obtained in a solid form, for example, by evaporation of the aqueous slurry to dryness, dropping the aqueous slurry on a heated surface for drying or spray drying of the aqueous slurry, or filtration or centrifugal separation of the aqueous slurry.

For the preparation of the precursor oxide, it is possible to adjust the pH of the solution, or to control the crystal structure of the resulting precursor oxide, by conducting the hydrothermal treatment in the presence of ammonium ions or ammonium type ions such as organic ammonium ions.

The precursor oxide obtained by the process of the present invention may be used as a catalyst by itself or as an active component of a catalyst, or as a precursor thereof, for the production of maleic anhydride by vapor phase oxidation of a hydrocarbon having at least 4 carbon atoms such as butane, butene or 1,3-butadiene.

For example, the precursor oxide itself may be molded, if necessary by using a molding additive, into pellets or any other catalyst form, so that it is useful as a fixed bed catalyst. Otherwise, the precursor oxide as an active component may be molded together with a carrier or other adjuvant, if necessary by using a molding additive, into pellets or other catalyst form, so that it may be used as a fixed bed catalyst. When the precursor oxide is formed into a catalyst, the obtained catalyst is usually calcined in a reactor at a temperature of from 400° to 600° C. and converted to the form of a calcined oxide and thus activated, and then it is used for the reaction. As the atmosphere for calcination, an inert gas such as nitrogen or argon, air, air diluted with an inert gas, or air containing butane or butene, may suitably be employed. Further, the activation by such calcination can be conducted by means of a suitable calcination furnace out of the reactor.

As mentioned above, by the calcination of the precursor oxide, the calcined oxide is obtainable. The calcining temperature is usually from 350° to 800° C., preferably from 400° to 600° C. The atmosphere for calcination is the same as described above with respect to the calcination of the catalyst containing the precursor oxide.

The calcined oxide thereby obtained, may be used by itself as a catalyst, or as an active component of a catalyst, useful for the production of maleic anhydride by gas phase oxidation of a hydrocarbon having at least 4 carbon atoms such as butane, butene or 1,3-butadiene.

For example, the calcined oxide itself may be molded, if necessary by using a molding assistant, into pellets or other catalyst form, so that it may be used as a fixed bed catalyst. Otherwise the calcined oxide may be molded as an active component together with a carrier or other adjuvant, if necessary by using a molding additive, into pellets or other catalyst form, so that it may be used as a fixed bed catalyst. Even such a catalyst containing the calcined oxide, may be activated by calcination in the same manner as in the case of the catalyst containing the precursor oxide.

Further, the above precursor oxide or (preferably) the calcined oxide may be used as a fluidized bed catalyst, by molding it together with a carrier or other adjuvant into the form of a fluidized bed catalyst such as fine spherical particles. As such a molding method, a spray drying method is suitable. Particularly preferred for this purpose is a method wherein a first component composed of the precursor oxide or the calcined oxide, a second component composed of an aqueous solution containing vanadium and phosphorus (preferably at least a part thereof being in the form of vanadyl phosphate) and a third component composed of silica sol, are mixed to obtain an aqueous slurry, and the slurry is spray-dried, and the resulting solid particles are calcined (see Japanese Unexamined Patent Publications No. 170542/1983 and No. 170543/1983). In such a case, the first component is preferably pulverized into fine powder at a stage prior to the preparation of the aqueous slurry. For this purpose, a suitable pulverization apparatus such as a hammer mill, a jet mill, a colloid mill or a sand grinder, may be used, and the pulverization may be conducted in a wet system or in a dry system usually to obtain a particle size of not more than 10 μm, preferably not more than 5 μm. For the calcination, a calcination furnace of any optional type such as a muffle furnace, a rotary kiln or a fluidized calcination furnace, may be employed. The atmosphere for the calcination is the same as described with respect to the calcination of the catalyst containing the precursor oxide. The fluidized bed catalyst thus obtained is excellent in the catalytic activity, flowabilities and strength.

The solid particles obtained by the above-mentioned spray drying, may be shaped into pellets or other catalyst form and may be used as a fixed bed catalyst.

The catalyst thus obtained is suitable for use for the production of maleic anhydride by gas phase catalytic oxidation from a hydrocarbon having at least 4 carbon atoms. As the hydrocarbon, n-butane, 1-butene, 2-butene, 1,3-butadiene or a mixture thereof is preferably employed. Particularly advantageous from the economical viewpoint, are n-butane and butene. These materials can readily be obtained, for example, by the separation from a natural gas, by the separation from the cracking product of naphtha, or by FCC reaction.

The gas phase contact reaction may be conducted in a fluidized bed system or in a fixed bed system. As the oxidizing agent, air or a molecular oxygen-containing gas may be used. The hydrocarbon material is usually from 0.5 to 10% by volume, preferably from 1 to 5% by volume, and the oxygen concentration is usually within a range of from 10 to 30% by volume. The reaction temperature is usually within a range of from 300° to 550° C., preferably from 350° to 500° C., and the reaction pressure is usually atmospheric pressure or an elevated pressure within a range of from 0.05 to 10 kg/cm$^2$.

Now, the present invention will be described in further detail with reference to Examples. However, it should be understood that the present invention is by no means restricted by such specific Examples.

EXAMPLE 1

Into a 300 ml beaker, 50 g of deionized water, 27.7 g (240 mmol) of 85% $H_3PO_4$, 3.13 g (50 mmol) of 80% $N_2H_4 \cdot H_2O$, 2.70 g (10 mmol) of $FeCl_3 \cdot 6H_2O$, 1.76 g (20 mmol) of N,N'-dimethylethylenediamine were charged and stirred. When the solution became uniform, 17.5 g (190 mmol) of $V_2O_5$ was gradually added, and the entire amount was dissolved. The solution was adjusted to 100 g, put into a container made of Teflon and subjected to hydrothermal treatment at 150° C. for 12 hours in the closed pressure container. Upon cooling, a blue colored aqueous slurry was obtained. This slurry was filtered, then washed with acetone and dried in a dryer at 130° C. for one day to obtain catalyst A.

COMPARATIVE EXAMPLE 1

Catalyst B was prepared in the same manner as in Example 1 except that $FeCl_3$ and N,N'-dimethylethylenediamine were not added.

COMPARATIVE EXAMPLE 2

Catalyst C was prepared in the same manner as in Example 1 except that N,N'-dimethylethylenediamine was not added.

COMPARATIVE EXAMPLE 3

Catalyst D was prepared by physically mixing 5 mol % of $FePO_4$ to catalyst B prepared in Comparative Example 1.

EXAMPLE 2

Catalyst E was prepared in the same as in Example 1 except that 10 mmol of $Fe(NO_3)_3$ was used instead of $FeCl_3$.

EXAMPLE 3

Into a 200 ml four-necked flask, 50 g of deionized water, 3.13 g (50 mmol) of 80% $N_2H_4 \cdot H_2O$, 17.4 g (190 mmol) of $V_2O_5$ were charged and refluxed for 2 hours. Then, 2.70 g (10 mmol) of $FeCl_3 \cdot 6H_2O$ and 1.76 g (20 mmol) of N,N'-dimethylethylenediamine were added thereto, and the mixture was refluxed further for 2 hours. Then, 27.7 g (240 mmol) of 85% $H_3PO_4$ was added. A greenish blue color solution was obtained. The solution was further refluxed for 30 minutes, and then hydrothermal treatment was conducted in the same manner as in Example 1. The subsequent steps were carried out in the same manner as in Example 1 to obtain catalyst F.

EXAMPLE 4

Catalyst G was prepared in the same manner as in Example 3 except that 3.13 g (50 mmol) of ethylene glycol was used instead of N,N'-dimethylethylenediamine.

EXAMPLE 5

Catalyst H was prepared in the same manner as in Example 4 except that 50 mmol of 2,4-pentanediol was used instead of ethylene glycol.

TEST EXAMPLE 1

(Comparative test of catalysts of Examples 1 to 5 and Comparative Examples 1 to 3)

By using the above-mentioned respective catalysts (Catalysts A to H), gas phase catalytic oxidation of N-butane was conducted. Each catalyst was calcined in a nitrogen atmosphere, molded into tablets and then pulverized to a particle size of from 24 to 60 mesh. 1 ml of each catalyst was packed into a quartz reactor tube and heated to 540° C. in a nitrogen atmosphere, and then a reaction gas comprising 4% of n-butane, 20% of oxygen and 76% of nitrogen was supplied, and the reaction was conducted. The flow rate of the reaction gas was 1 l/hr, and SV was 1,000 hr$^{-1}$. The analysis was conducted by gas chromatography connected on-line. The gas at the outlet of the reactor tube was sampled, and then the temperature was lowered every 15° C., and the catalytic activities at each temperature were examined, and the maximum yield of maleic anhydride and the optimum reaction temperature giving the maximum yield, were obtained. For the evaluation of the catalytic activities, the reaction was conducted by repeating the same procedure with the same catalyst, and the results of the third trial were compared. The results are shown in Table 1. Catalyst B of Comparative Example 1 represents divanadyl pyrophosphate having no accelerator incorporated, and Comparative Example 2 represents a case where iron was added in the absence of a coordinate compound during the preparation by hydrothermal treatment. It is evident that simple addition of iron is not adequate, and excellent accelerating effects are obtainable for the first time by conducting the hydrothermal treatment in the presence of the coordinate compound.

TABLE 1

| | | Catalytic Activities for reaction | | |
|---|---|---|---|---|
| | Catalyst | Optimum temperature for reaction | Conversion of butane | Yield of maleic anhydride |
| Example 1 | A | 467° C. | 85.0% | 51.8% |

TABLE 1-continued

| Catalyst | | Catalytic Activities for reaction | | |
|---|---|---|---|---|
| | | Optimum temperature for reaction | Conversion of butane | Yield of maleic anhydride |
| Comparative Example 1 | B | 469° C. | 85.0% | 47.4% |
| Comparative Example 2 | C | 470° C. | 84.8% | 46.2% |
| Comparative Example 3 | D | 444° C. | 79.2% | 45.2% |
| Example 2 | E | 477° C. | 88.0% | 51.7% |
| Example 3 | F | 470° C. | 86.2% | 52.0% |
| Example 4 | G | 441° C. | 89.4% | 54.5% |
| Example 5 | H | 428° C. | 86.5% | 51.0% |

EXAMPLES 6 to 8

Catalyst I (Example 6), Catalyst J (Example 7) and Catalyst K (Example 8) were prepared in the same manner as in Example 4 except that 10 mmol of $NiCl_2 \cdot 6H_2O$ (Example 6), $CrCl_3 \cdot 6H_2O$ (Example 7) or $CoCl_3 \cdot 6H_2O$ (Example 8) was used, respectively, instead of $FeCl_3 \cdot 6H_2O$.

TEST EXAMPLE 2

(Comparative test of catalysts of Examples 4 and 6 to 8 and Comparative Example 1)

By using Catalysts G, I to K and Catalyst B, gas phase catalytic oxidation of n-butane was conducted. Each catalyst was calcined in a nitrogen atmosphere, molded into tablets and pulverized to a particle size of from 24 to 60 mesh. 1 ml of each catalyst was packed into a quartz reactor tube and heated to 510° C. in a nitrogen atmosphere, and the reaction was conducted by supplying a reaction gas comprising 4% of n-butane, 20% of oxygen and 76% of nitrogen. The flow rate of the reaction gas was 1 l/hr, and SV was 1,000 hr$^{-1}$. The analysis was conducted by gas chromatography connected on-line. The gas at the outlet of the reactor tube was sampled, and the catalytic activities for the reaction were examined. The results are shown in Table 2. With respect to Catalysts G, I, K and B, the catalytic activities for reaction at 420° C. are shown, and with respect to Catalyst J, the catalytic activities for reaction at 400° C. are shown.

TABLE 2

| | | Catalytic Activities for reaction | |
|---|---|---|---|
| | Catalyst | Conversion of butane | Yield of maleic anhydride |
| Example 4 | G | 87% | 51% |
| Example 6 | I | 58% | 40% |
| Example 7 | J | 80% | 45% |
| Example 8 | K | 76% | 45% |
| Comparative Example 1 | B | 52% | 37% |

TEST EXAMPLE 3

(Test of catalyst of Example 4)

Catalyst G prepared in Example 4 (hereinafter referred to as "first component") was made into a fluidized bed catalyst in accordance with the following procedure, and the catalytic activities for reaction were examined.

(1) 1 mol of each of phosphoric acid, oxalic acid and $V_2O_5$ was dissolved in 300 g of deionized water under heating and boiled for 10 minutes. Then, deionized water was added to adjust the amount to 500 g. This solution (hereinafter referred to as "second component") contained 30.7% of $V_2O_4 + P_2O_5$.

(2) The first component, the second component and a commercially available colloidal silica solution having a concentration of 20% (third component) were charged in a weight ratio of 70%, 25% and 5%, respectively. Deionized water was mixed thereto to obtain a uniform slurry with the slurry weight ratio of 35%. Then, the slurry was charged in a wet system pulverizer and subjected to pulverization to fine powder at room temperature. During the preparation of the slurry, phosphoric acid was added to bring the ratio of P/V+Fe to 1.05. The average fine particle size in the slurry after the pulverization treatment was measured and found to be about 0.2 μm.

(3) The slurry subjected to pulverization treatment to fine powder was recovered, spray-dried and then calcined at 600° C. in nitrogen to obtain a fluidized bed catalyst (Catalyst L).

(4) Gas phase catalytic oxidation of n-butane was conducted in the same manner as in Test Example 1 except that Catalyst L was used as the catalyst. The results are shown in Table 3.

TEST EXAMPLE 4

(Test of the catalyst of Example 4)

The test was conducted in the same manner as in Test Example 3 except that the charging ratio of the first component, the second component and the third component in Step (3) was changed to 70%, 20% and 10%, respectively, and the P/V+Fe ratio was changed to 1.00. The results are shown in Table 3.

TABLE 3

| | Optimum temperature for reaction | Conversion of butane | Yield of maleic anhydride |
|---|---|---|---|
| Test Example 3 | 466° C. | 89.8% | 56.1% |
| Test Example 4 | 450° C. | 90.7% | 60.1% |

As described in the foregoing, according to the present invention, it is possible to obtain a crystalline oxide of vanadium-phosphorus system and a catalyst containing it, which have excellent catalytic activities and which are capable of providing improved yield in the gas phase catalytic oxidation reaction.

We claim:

1. A process for producing a crystalline oxide of vanadium-phosphorus system, which comprises hydrothermally treating at a temperature of 110°-250° C. in a closed container an aqueous medium containing (1) a tetravalent vanadium compound, (2) a pentavalent phosphorus compound, (3) a coordinate compound having at least two ligand atoms selected from the group consisting of a polyhydric alcohol, and, a polybasic organic acid and (4) a compound of at least one metal element selected from the group consisting of iron, nickel, cobalt and chromium, to form a crystalline oxide of vanadium-phosphorus system having a X-ray diffraction pattern shown in Table A:

TABLE A

| X-ray diffraction peaks (Anticathode: Cu—Kα) 2θ (±0.2°) | | | |
|---|---|---|---|
| 15.6° | 19.7° | | 24.3° |
| 27.2° | 28.8° | 30.5° | 33.8° |

TABLE B

| X-ray diffraction peaks (Anticathode: Cu—Kα) | | |
|---|---|---|
| 14.2° | 15.7° | 18.5° |
| 23.0° | 28.4° | 30.0° |
| 33.7° | 36.8° | | wherein the coordinate compound is used in a molar ratio of from 0.01 to 1.0 to vanadium, the atomic ratio of phosphorus/vanadium is from 0.5 to 2.0, and the atomic ratio of the compound of at least one metal element to vanadium is from 0.001 to 1.0.

2. The process according to claim 1, wherein the tetravalent vanadium compound is obtained by reducing a pentavalent vanadium compound with a reducing agent.

3. The process according to claim 1, wherein the tetravalent vanadium compound and the pentavalent phosphorus compound are obtained by the oxidation reduction reaction of a pentavalent vanadium compound with a trivalent phosphorus compound.

4. The process according to claim 1, wherein the compound of the metal element is selected from the group consisting of inorganic and organic salts of iron, cobalt, nickel and chromium.

5. The process according to claim 1, wherein the polyhydric alcohol is selected from the group consisting of ethylene glycol, 1,4-butanediol, 2,4-pentanediol and pinacol.

6. The process according to claim 1, wherein the polybasic organic acid is selected from the group consisting of tartaric acid, oxalic acid and ethylenediamine tetraacetic acid.

7. The process according to claim 1, wherein the coordinate compound is used in a molar ratio of from 0.1 to 0.5 to vanadium.

8. A process for producing a catalyst containing a crystalline oxide of vanadium-phosphorus system, which comprises shaping the crystalline oxide of vanadium-phosphorus system as defined in claim 1 into a catalyst form.

9. A process for producing a crystalline oxide of vanadium-phosphorus system, which comprises calcining at a temperature of from 400° to 600° C. a crystalline oxide of vanadium-phosphorus system obtained by hydrothermally treating at a temperature of 110°–250° C. in a closed container an aqueous medium containing (1) a tetravalent vanadium compound, (2) a pentavalent phosphorus compound, (3) a coordinate compound having at least two ligand atoms selected from the group consisting of a polyhydric alcohol, and, a polybasic organic acid and (4) a compound of at least one metal element selected from the group consisting of iron, nickel, cobalt and chromium, to form a crystalline oxide of vanadium-phosphorus system having a X-ray diffraction pattern shown in Table A:

TABLE A

| X-ray diffraction peaks (Anticathode: Cu—Kα) 2θ (±0.2°) | | | |
|---|---|---|---|
| 15.6° | 19.7° | | 24.3° |
| 27.2° | 28.8° | 30.5° | 33.8° | to form a crystalline oxide of vanadium-phosphorus system having an X-ray diffraction pattern shown in Table B:

TABLE B

| X-ray diffraction peaks (Anticathode: Cu—Kα) | | |
|---|---|---|
| 14.2° | 15.7° | 18.5° | wherein the coordinate compound is used in a molar ratio of from 0.01 to 1.0 to vanadium, the atomic ratio of phosphorus/vanadium is from 0.5 to 2.0, and the atomic ratio of the compound of at least one metal element to vanadium is from 0.001 to 1.0.

10. The process according to claim 9, wherein the tetravalent vanadium compound is obtained by reducing a pentavalent vanadium compound with a reducing agent.

11. The process according to claim 9, wherein the tetravalent vanadium compound and the pentavalent phosphorus compound are obtained by the oxidation reduction reaction of a pentavalent vanadium compound with a trivalent phosphorus compound.

12. The process according to claim 9, wherein the compound of the metal element is selected from the group consisting of inorganic and organic salts of iron, cobalt, nickel and chromium.

13. The process according to claim 9, wherein the polyhydric alcohol is selected from the group consisting of ethylene glycol, 1,4-butanediol, 2,4-pentanediol and pinacol.

14. The process according to claim 9, wherein the polybasic organic acid is selected from the group consisting of tartaric acid, oxalic acid and ethylenediamine tetraacetic acid.

15. The process according to claim 9, wherein the coordinate compound is used in a molar ratio of from 0.1 to 0.5 to vanadium.

16. A process for producing a catalyst containing a crystalline oxide of vanadium-phosphorus system, which comprises calcining at a temperature of from 400° to 600° C. a crystalline oxide of vanadium-phosphorus system obtained by hydrothermally treating at a temperature of 110°–250° C. in a closed container an aqueous medium containing (1) a tetravalent vanadium compound, (2) a pentavalent phosphorus compound, (3) a coordinate compound having at least two ligand atoms selected from the group consisting of a polyhydric alcohol, and, a polybasic organic acid and (4) a compound of at least one metal element selected from the group consisting of iron, nickel, cobalt and chromium, to form a crystalline oxide of vanadium-phosphorus system having a X-ray diffraction pattern shown in Table A:

TABLE B-continued

| X-ray diffraction peaks (Anticathode: Cu—Kα) | | |
| --- | --- | --- |
| 23.0° | 28.4° | 30.0° |
| 33.7° | 36.8° | | and then shaping the crystalline oxide into a catalyst form, wherein the coordinate compound is used in a molar ratio of from 0.01 to 1.0 to vanadium, the atomic ratio of phosphorus/vanadium is from 0.5 to 2.0, and the atomic ratio of the compound of at least one metal element to vanadium is from 0.001 to 1.0.

* * * * *